United States Patent
Backman et al.

[11] Patent Number: 5,957,865
[45] Date of Patent: Sep. 28, 1999

[54] FLEXIBLE CATHETER GUIDEWIRE

[75] Inventors: Kent Backman, Holladay; Jerrold Foote, Salt Lake City, both of Utah

[73] Assignee: Merit Medical Systems, Inc., South Jordan, Utah

[21] Appl. No.: 08/937,716

[22] Filed: Sep. 25, 1997

[51] Int. Cl.[6] ................................................. A61B 5/103
[52] U.S. Cl. ............................................................ 600/585
[58] Field of Search ........................... 600/433–435, 600/585

[56] References Cited

U.S. PATENT DOCUMENTS

| | | | |
|---|---|---|---|
| Re. 33,911 | 5/1992 | Samson et al. | 128/772 |
| 3,789,841 | 2/1974 | Antoshkiw | 128/2.05 R |
| 4,538,622 | 9/1985 | Samson et al. | 128/772 |
| 4,554,929 | 11/1985 | Samson et al. | 128/772 |
| 4,721,117 | 1/1988 | Mar et al. | 128/772 |
| 4,846,186 | 7/1989 | Box et al. | 128/657 |
| 4,884,579 | 12/1989 | Engelson | 128/772 |
| 5,069,217 | 12/1991 | Fleischhecker | 600/585 |
| 5,259,393 | 11/1993 | Corso, Jr. et al. | 128/772 |
| 5,267,574 | 12/1993 | Viera et al. | 128/772 |
| 5,333,620 | 8/1994 | Moutafis et al. | 128/772 |
| 5,365,942 | 11/1994 | Shank | 128/772 |
| 5,372,144 | 12/1994 | Mortier et al. | 128/772 |
| 5,429,139 | 7/1995 | Sauter | 128/772 |
| 5,452,726 | 9/1995 | Burmeister et al. | 128/772 |
| 5,497,783 | 3/1996 | Urick et al. | 128/772 |
| 5,497,786 | 3/1996 | Urick | 128/772 |
| 5,498,250 | 3/1996 | Prather | 604/280 |
| 5,520,194 | 5/1996 | Miyata et al. | 600/585 |

*Primary Examiner*—Max Hindenburg
*Attorney, Agent, or Firm*—Workman, Nydegger, Seeley

[57] ABSTRACT

A flexible catheter guidewire that comprises an elongate flexible core wire, a cylindrical, thin-walled hollow tube, and a coil spring. The core wire consists of a main section, a tapered section, and a flattened tip. The main section of the core wire has a predetermined uniform diameter. The tapered section of the core wire has a progressively reduced outer diameter. The flattened tip has a substantially rectangular cross-section. The flattened tip has a first end that is attached to the tapered section of the core wire and a second end. The flattened tip decreases in thickness from the first end of the flattened tip to the second end of the flattened tip. The hollow tube is disposed around the tapered section of core wire. The hollow tube has a substantially uniform inner diameter. A gap is formed between the inner surface of the hollow tube and the outer surface of the tapered section. A coil spring constructed of a radiopaque material is attached to the core wire and is disposed around the flattened tip.

12 Claims, 2 Drawing Sheets

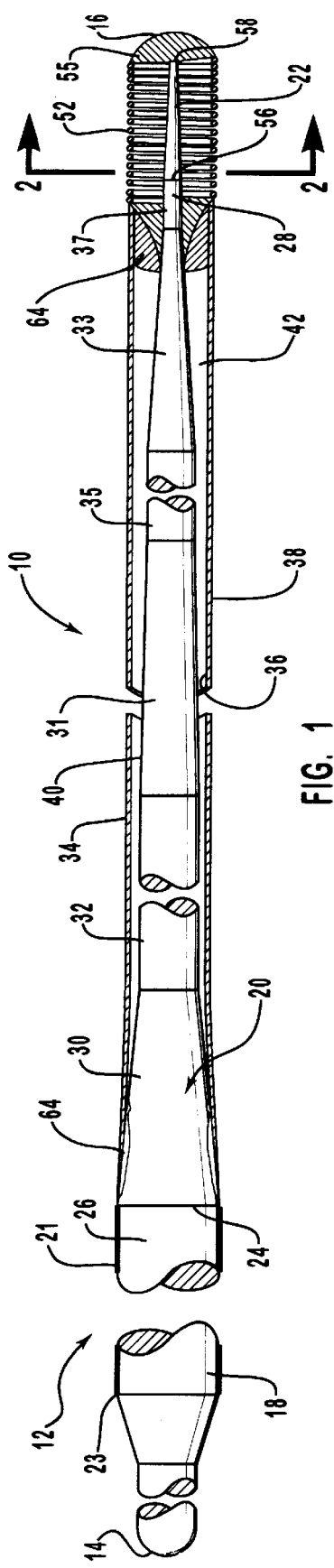
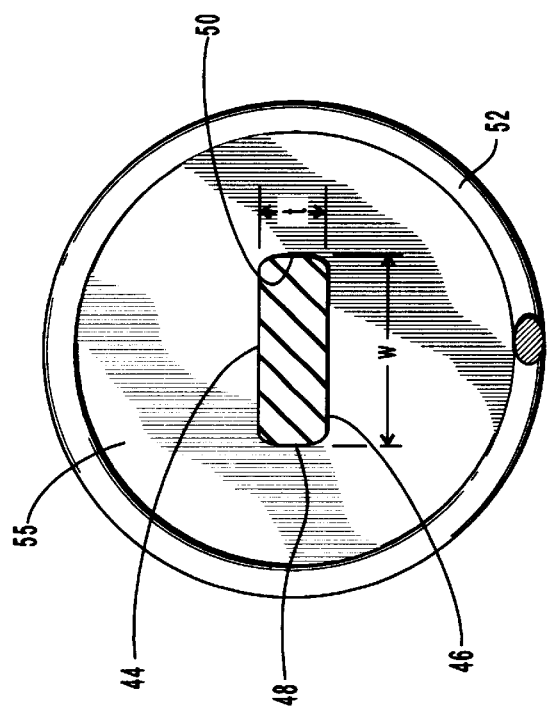

FLEXIBLE CATHETER GUIDEWIRE

BACKGROUND OF THE INVENTION

1. Field of the Invention

This invention relates to a guidewire for facilitating the placement of a catheter within a patient's cardiovascular system. More particularly, the present invention is directed to a flexible, elongate guidewire having enhanced steering properties, that is especially suitable for use in connection with the positioning a balloon dilation catheter in a percutaneous transluminal coronary angioplasty procedure.

2. The Relevant Technology

Catheters are used in a wide variety of medical situations to deliver and administer medicaments to a specific site within a patient's body. Depending on the particular type of medical procedure involved, there is often a need to position a catheter within the patient's body at a specific location, so that a targeted diseased area can then be treated. One example of a medical procedure that requires extremely accurate placement of a catheter is known as percutaneous transluminal coronary angioplasty, or PTCA, which involves the treatment of a narrowed coronary artery caused by a stenosis. In this procedure, a balloon dilation catheter is introduced into the patient's body via a suitable access site, and then advanced through the vasculature until the inflatable portion of the catheter (usually located at the distal end of the catheter) is positioned adjacent to the stenosis that is to be treated. The balloon is then inflated to a predetermined pressure so as to compress the stenosis, and thereby dilate the narrowed vessel.

The nature of a PTCA procedure is such that there is a need to be able to accurately and precisely maneuver the catheter through the patient's vascular system, which typically involves the need to negotiate a series a sharp bends and/or junctions. Typically, this advancement and positioning of the catheter is accomplished with the aid of an elongate, flexible guidewire. The guidewire is first inserted into the patient's vasculature and then the guidewire tip is advanced through the appropriate vessel until it is positioned at a point just beyond the stenosis. The catheter is then advanced over the guidewire to a point where the balloon portion of the catheter is positioned adjacent to the stenosis. Typically, the distal portion of the guidewire is comprised of a radiopaque material such that the advancement and positioning of the guidewire, relative to the stenosis, can be observed by the practitioner fluoroscopically.

Given the nature of the portion of the vascular system typically treated in a PTCA procedure, the PTCA guidewire must be flexible enough so that it can traverse the turns and bends encountered as it is guided to the target vessel. At the same time, the guidewire must be relatively torsionally rigid to allow the guidewire to be manipulated and advanced through the vessel by the practitioner from an external access site. Also, while the distal tip end of the guidewire must be sufficiently flexible so as to be maneuvered through irregular paths, it must be capable of being moved through a partially occluded vessel without kinking or breaking.

The maneuverability and flexibility of a guidewire is often improved by reducing the diameter of the core wire at the distal end. While this improves the flexibility of the distal end of the wire, it also reduces the wire's strength, leaving it susceptible to kinking and/or breaking within the patient's blood vessel. Moreover, depending on the technique used, the reduction in diameter can result in a guidewire having discontinuities in its surface. This can result in trauma to the interior walls of the blood vessel as the guidewire is advanced, and/or may promote the formation of blood clots.

One approach used to address these problems is to wrap a wire spring coil about the distal end of the reduced-diameter portion of the guidewire. The spring coil permits the reduced-diameter portion of the wire to retain its flexibility and at the same time add some structural rigidity to the wire to reduce the risk of breaking and kinking within the blood vessels. However, the approach is not entirely satisfactory in that the outer surface formed by the coil is somewhat irregular and has a relatively higher coefficient of friction than other portions of the guidewire. Again, this can result in trauma to the blood vessel, can result in increased formation of blood clots, and can inhibit the ability to advance the wire through the blood vessel and/or catheter.

As an alternative to using a spring coil, some guidewire designs utilize a plastic coating to completely encase at least a portion of the the tapered distal end of the guidewire's core wire. While such an approach results in a smoother outer surface, the approach also lessens the overall flexibility of the distal end because the plastic, which is stiffer than the wire, completely encases the tapered wire portion. This decrease in flexibility detracts from the overall steerability of the guidewire.

Thus, there is a need for a PTCA guidewire that retains sufficient flexibility in the distal end, and at the same time is not subject to breaking or kinking. Further, the guidewire distal end should have a continuously smooth and uniform outer surface. Finally, the wire should have superior steering characteristics so as to be capable of being maneuvered through the types of blood vessels typically encountered in a PTCA procedure.

SUMMARY AND OBJECTS OF THE INVENTION

It is a primary object of the present invention to provide an elongate, flexible guidewire, suitable for accurately positioning a catheter at a target site within blood vessel, such as would typically be encountered in a PTCA procedure.

Another object of the present invention is to provide a guidewire that is flexible enough so that it can be accurately maneuvered and advanced through a patient's coronary vasculature to a specific target site.

Still another object of the present invention is to provide a guidewire that is sufficiently rigid so as to be capable of being advanced into a patient's vasculature to a particular target point, without kinking or breaking.

Another object of the present invention is to provide a guidewire having an outer surface that is consistently lubricious along substantially the entire length of the guidewire.

Yet another object of the present invention is to provide a guidewire having a distal end that is more flexible than the rest of the guidewire so as to further facilitate the advancement and positioning of the guidewire through a blood vessel to a target site.

Another object of the present invention is to provide a guidewire having a distal end portion that, in addition to being flexible, is also resistant to kinking and breaking.

Yet another object of the present invention is to provide a guidewire having a distal end that has predefined bending characteristics that can be used to orientate the tip in a manner that aids in the advancement and positioning of the guidewire to a target site within a specific blood vessel.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a flexible catheter guidewire for insertion into a blood vessel to aid in the positioning of a catheter is disclosed. The guidewire is particularly suitable for use in the advancement of the type of balloon dilation catheter that is typically used in a percutaneous transluminal coronary angioplasty (PTCA) procedure. In the preferred embodiment, the guidewire comprises an elongate flexible core wire having a proximal, cylindrically shaped main section, a more distally located tapered intermediate section, and at the extreme distal end, a more flexible tip section.

In a preferred embodiment, the main section of the core wire has a uniform outer diameter, and the tapered intermediate section of the core wire extends from the main section and has a progressively reduced outer diameter so as to have increased flexibility. The flattened tip end section extends from the tapered intermediate section and has a substantially rectangular cross-sectional shape so as to be even more flexible in particular directions.

In the preferred embodiment, a cylindrical, thin-walled hollow tube is attached at both of its ends to the surface of the core wire, and is disposed around the tapered intermediate section of core wire. The thin wall of the tube has a constant and uniform thickness along the length of the tube. As such, the inner diameter of the hollow tube is also uniform along the length of the tube, thereby forming a spaced apart relationship between the inner surface of the tube, and the outer surface of the intermediate tapered section. The size of this gap progressively increases as the intermediate section tapers down in diameter. The outer diameter of the hollow tube is substantially equal to the outer diameter of the proximal main section of the core wire. In this way, the outer diameter of the guidewire is substantially uniform along its entire length. Also, the tube is preferably composed of a polymer material so as to provide a continuously smooth and lubricious surface along the length of the guidewire, thereby improving the guidewire's ability to be advanced and maneuvered through a blood vessel. Also, the geometry of the tube also improves the steerability of the guidewire. Since the tube is disposed about the tapered intermediate section, it prevents the guidewire from kinking and/or breaking as it is advanced through a blood vessel. At the same time, the spaced apart relationship between the inner surface of the tube and the outer surface of the coil wire along the intermediate section permits the guidewire to retain a maximum amount of flexibility along this portion. Again, this flexibility enhances the guidewire's ability to be maneuvered through tortious blood vessel paths.

The geometry of the distal end tip also enhances the guidewire's maneuverability. Since the distal end is flattened, or otherwise formed into a rectangular cross-section, the distal end has yet even greater flexibility in directions substantially perpendicular to the flattened surface. This allows the guidewire to engage and maneuver through particular bends in the vasculature encountered by the guidewire and permits the practitioner to steer the guidewire with more precision. Also, the flattened configuration results in a distal tip that resists bending in directions substantially parallel to the flat planar surfaces. Again, this bending characteristic can be utilized by the practitioner as the guidewire is maneuvered through the blood vessels. Finally, the flattened geometry of the distal tip permits the practitioner to pre-bend the distal tip in a particular configuration depending on the known characteristics of the particular region of vasculature to be traversed. The flattened property of the distal tip ensures that the bent configuration is retained as the guidewire is advanced. When a particular bend or junction is encountered, the practitioner can rotate the guidewire at its proximal end and align the pre-bent tip in an appropriate direction so as to traverse the particular blood vessel junction. Again, this greatly enhances the guidewire maneuverability.

A small coil spring, preferably made of a radiopaque material, is attached to the core wire and is disposed around the flattened tip section. The coil spring provides the flattened portion with additional strength so that the tip does not break or kink. At the same time, the coil allows the tip to retain its flexibility. Also, the outer diameter of the coil is substantially equal to the outer diameter of the thin-walled tube and the proximal main section of the wire. Again, this maintains the uniform diameter along the entire length of the guidewire. Also, in the preferred embodiment, the outer surface of the wire strands of the coil are coated with a lubricious material, thereby maintaining the continuous and uniform lubricity along the entire length of the guidewire. Preferably, the spring coil is constructed of a radiopaque material so that the practitioner can observe the tip fluoroscopically as it is being advanced within the patient.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 1 is a partial cross-sectional side elevation view of one embodiment of a floppy guidewire incorporating teachings of the present invention;

FIG. 2 is an enlarged cross-sectional view of the distal portion of the floppy guidewire of FIG. 2 taken along section line 2—2;

DETAILED DESCRIPTION OF THE PREFERRED EMBODIMENTS

Figure 3:
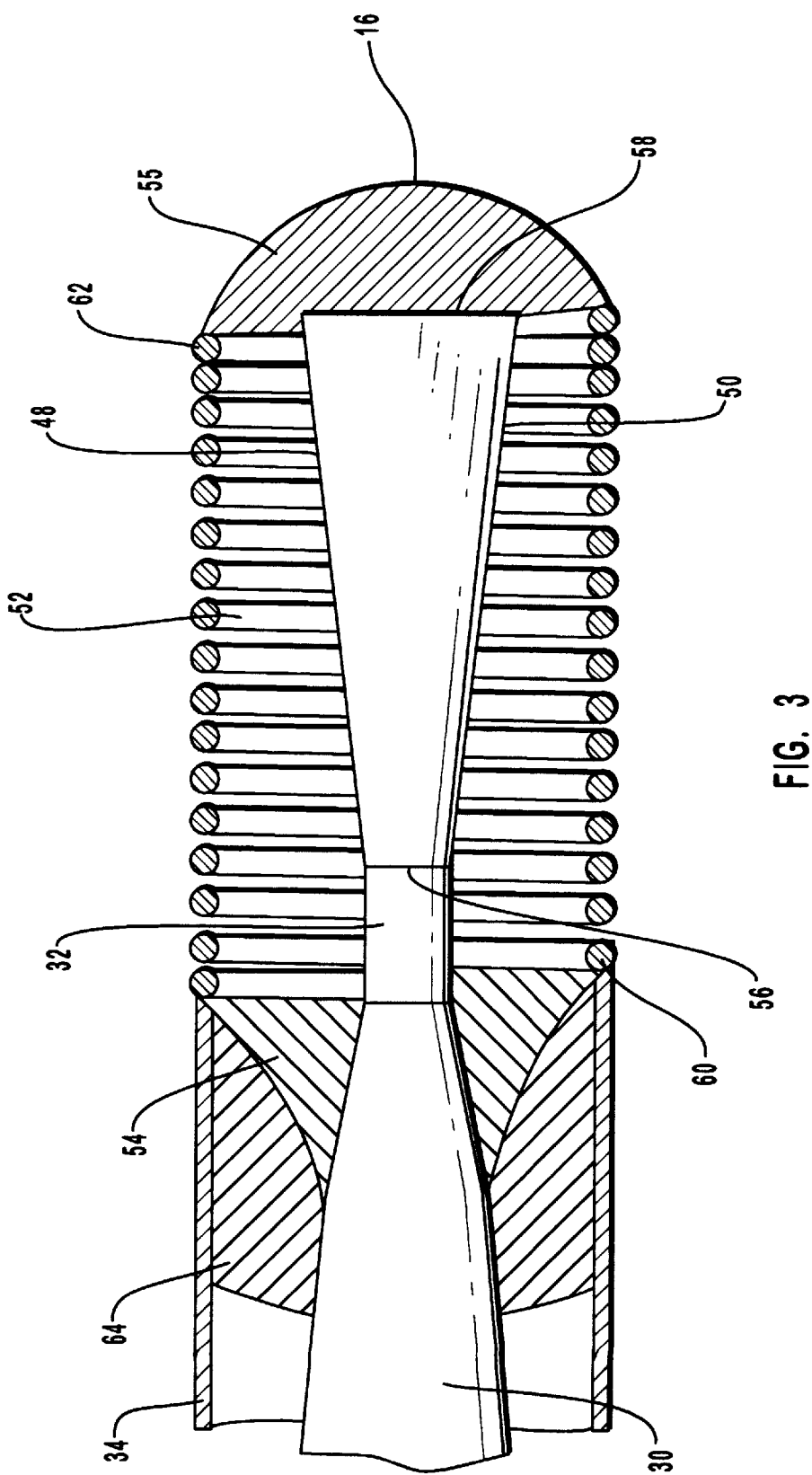
FIG. 3 is an enlarged partial cross-sectional elevation view of the distal tip of the embodiment of a floppy guidewire of FIG. 1.

The present invention relates to a floppy guidewire used to introduce a catheter into a target site in the cardiovascular system. FIG. 1 illustrates an example of one preferred embodiment of a guidewire, designated generally at 10. Guidewire 10 includes an elongate, flexible core wire 12, which is preferably constructed of No. 304 stainless steel or similar material. The core wire 12 has a proximal end 14 and a distal end 16, and has a main cylindrical section 18, a more distally located tapered intermediate section 20, and at the extreme distal end, an end section 22. In a preferred embodiment, the overall length of core wire 12 is approximately 175 centimeters, but it will be appreciated that the length may vary depending on the specific application, and for most procedures will range from about 150 centimeters to 300 centimeters.

The main section 18 of core wire 12 is cylindrical in cross-section, and has a substantially uniform diameter extending from proximal region 23 to a distal region 24, which in one preferred embodiment is about .0135 inches. Preferably, the main cylindrical section is coated with a lubricious, medically inert, coating such as TEFLON®, which facilitates insertion of the wire within a blood vessel and the catheter lumen. Main section 18 makes up a major portion of core wire 12.

Extending from the distal end 24 of the main cylindrical section 18 is a tapered intermediate section 20 of core wire 12. Intermediate section 20 is configured so as to have a progressively reduced outer diameter toward the distal end of the guidewire 10, which is shown in FIG. 1. The flexibility of tapered section 20 increases as the diameter of tapered section 20 decreases. As is illustrated in the embodiment of FIG. 1, this tapered configuration is accomplished by way of several discrete tapered steps 30, 31 and 33, which progressively reduce the diameter of core wire 12. Each tapered step is followed by a corresponding cylindrical portion 32, 35 and 37, that each have a progressively reduced diameter. Alternatively, the reduction in diameter of intermediate section 20 could be accomplished with a single continuous taper, or with a smaller or larger number of discrete tapered steps.

As is further illustrated in FIG. 1, a cylindrical, thin-walled, hollow tube 34 is disposed around the tapered intermediate section 20. Preferably, hollow tube 34 comprises a flexible, lucent, polymer material and has a lubricious surface, such as a polyolefins or polyurethane material. As shown in FIG. 1, hollow tube 34 has a substantially uniform wall 38 thickness along the entire length of the tube and thus has a substantially uniform inner diameter and outer diameter along the length of the tube. In one preferred embodiment, the inner diameter of the tube is about 0.0115 to 0.009 inches. Since the inner diameter of the tube is substantially constant, the inner surface 36 of the hollow tube 34 and the outer surface 40 of tapered intermediate section 20 are in a spaced apart relationship so as to form a gap 42. As shown in FIG. 1, gap 42 becomes progressively larger as tapered section 20 tapers to progressively smaller diameters.

In addition, the outer diameter of tube 34 is substantially equal to that of the main cylindrical section 18 of core wire 12. This ensures a continuously and uniform smooth outer surface along the length of the guidewire 10, thereby permitting the guidewire 10 to be more easily advanced along a tortuous blood vessel path, and the catheter to be more easily advanced over guidewire 10. Also, the smooth surface reduces trauma to the blood vessel, and is more resistant to the formation of blood clots. Preferably, the lubricity of the outer surface 38 of tube 34 is approximately the same as that of the TEFLON® coated main cylindrical section 18, further aiding in the ability to advance the guidewire with respect to the blood vessel and the catheter.

In addition to providing a uniform, smooth outer surface, the hollow tube 34 reduces the risk of the intermediate section 20 breaking off during placement of the guidewire and catheter. At the same time, the tube's 34 thin-walled design allows the intermediate section 20 of the coil wire 20 to retain sufficient flexibility so as to be capable of negotiating the tortious path of a blood vessel typically encountered in the placement of a dilation catheter in a PTCA procedure. The flexibility is further enhanced due to the formation of the air gap 42, because it permits some independent movement and bending of the intermediate section 20 within the tube 34 as the guidewire is maneuvered within the turns of the vascular system.

Extending from the distal end of the intermediate section 20 is the flexible tip section 22. As illustrated in FIG. 1, tip section 22 comprises a first end 56 which is attached to the intermediate section 20 by way of cylindrical portion 32. Tip 22 is flattened, or otherwise preformed so as to have a substantially rectangular transverse cross-section, which is shown in more detail in FIG. 2.

Tip section 22 is mechanically flattened, or preformed, so as to have two opposed, substantially planar surfaces 44, 46. As is shown in the embodiment of FIG. 2, the flattening process used to flatten the tip 22 results in sides 48, 50 to be somewhat rounded due to the forces imposed by the flattening mechanism used, such as a mechanical press or forming dies. FIG. 1 illustrates how in one preferred embodiment, the tip 22 is flattened in a manner so as to have a tapered shape. Thus, the thickness of the tip gradually decreases towards the distal end 58 of tip section 22.

In a preferred embodiment, the thickness of flattened tip 22 (shown as the dimension "t" in FIG. 2) tapers from about 0.0026 inches at the first end 56 of flattened tip 22, to about 0.0009 inches at the distal end 58 of flattened tip 22. Also, the width of flattened tip 22 (shown as the dimension "w" in FIG. 2) gradually widens toward distal end 58 of tip 22. This widening of the tip 22 is better illustrated in FIG. 3, which shows how sides 48, 50 of flattened tip 22 flare outward in a triangular-like geometry.

The substantially rectangular cross-section of flattened tip 22 provides two distinct functions. First the substantially rectangular cross-section of flattened tip 22 results in greater flexibility of movement in a plane that is substantially perpendicular to planar surfaces 44, 46. In contrast, flattened tip 22 is much less flexible in other directions, and in particular, in a direction that is substantially perpendicular to sides 48, 50. This results in a guidewire having more predictable steering characteristics, thereby allowing the practitioner to more easily route the guidewire 10 to a specific target site.

Secondly, the flattened, rectangular shape of tip 22 also enhances the ability of flattened tip 22 to be bent into a specific orientation depending, for instance, on the particular vessel to be treated. Thus, flattened tip 22 can be pre-bent into a desired orientation, either during the guidewire's manufacture or by the surgeon at the time of the procedure. The angle and particular shape of the bend can be chosen in accordance with a particular use, and based upon the known location of the vessel to be treated and the path needed to reach the vessel. Flattened tip 22 that has been bent into a particular direction can be easily reoriented by the surgeon when it is being routed along cardiovascular system to the selected blood vessel, because torque supplied to proximal end 14 of guidewire 10 is transmitted along the length of guidewire 10 and enables the bent flattened tip 22 to be reoriented to point in the desired direction. Moreover, because the rectangular tip 22 resists distortion in directions perpendicular to the planes formed by sides 48, 50, the tip 22 is more apt to retain the pre-bent orientation given to it prior to insertion into the patient.

FIGS. 1–3 each illustrate how a flexible coil spring 52 is disposed about the tip section 22. Preferably, the coil spring 52 comprises a radiopaque material, such as a platinum and nickel alloy. This allows the tip of the guidewire 10 to be observed fluoroscopically while it is being maneuvered within the patient, so that the practitioner can accurately monitor the position of the tip.

Coil spring 52 extends from hollow tube 34 to distal end 16 of guidewire 10. Proximal end 60 of coil spring 52 is attached to tapered section 20 of core wire 12 by a solder or weld joint 54. A second solder joint 55 located at distal end 16 of guidewire 10 has a smooth, semi-hemispherical, exposed surface to enhance the ability to maneuver distal end 16 of guidewire 10 within a blood vessel and to prevent damage within the blood vessel. Solder joint 55 forms a smooth transition into distal end 62 of coil spring 52, and also secures the end 58 of flattened tip 22 to the end 62 of the spring 52.

Coil spring 52 allows flattened tip 22 to retain its flexibility and at the same time provides column strength to this section so as to prevent kinking and/or breaking of flattened tip 22. In a preferred embodiment, the first 2–4 coils of proximal end 60 of coil spring 52 and distal end 62 of coil spring 52 have about 0% pitch and closely abut one another. The remaining coils have about 25% pitch so that there is a slight gap between each adjacent coil wire. Other embodiments of coil spring 52 are equally effective in carrying out the intended function thereof Also, in the embodiment illustrated in FIGS. 1–3 the coil wires of the coil spring 52 are coated with a low friction polymer surface coating such as TEFLON®,or a similar low friction hydrophillic polymer surface coating. In this way, the lubricity of the coil wires of coil spring 52 is approximately the same as that of the tube 34 and the main section of the core wire 18. Also, the outer diameter of the coil spring 52 is substantially equal to that of the hollow tube 34 and the main section of the core wire 18. Again, this maintains the consistently uniform diameter along the entire length of the guidewire 12, maximizing the wire's ability to be advanced through a vessel and the catheter lumen, and minimizing any trauma to the blood vessel walls.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A flexible catheter guidewire comprising:
   a. an elongate flexible core wire comprising:
      a main section having a predetermined uniform diameter extending from a proximal and of the guidewire to a distal region of the guidewire;
      a tapered section extending distally from the main section and having a progressively reduced outer diameter;
      a flattened tip section extending distally from the tapered section;
   b. a coil spring attached to the core wire and disposed around the tip section; and
   c. a cylindrical, thin walled hollow tube attached at one end to the core wire beginning at the tapered section and extending continuously up to the coil spring where the other end of the thin-walled tube is attached to the core wire, the hollow tube having a substantially uniform inner diameter whereby a gap is formed between an inner surface of the hollow tube and an outer surface of the tapered section in order to provide a desired degree of flexibility and steerability, and the hollow tube having a substantially uniform outer diameter which corresponds to the outer diameter of the main section of the core wire in order to provide a continuously and uniformly smooth outer surface along the length of the guidewire from the main section to the coil spring.

2. A flexible catheter guidewire as recited in claim 1, wherein the flattened tip section comprises:
   a pair of opposing substantially planar surfaces; and
   a pair of side walls connecting the pair of planar surfaces, the pair of planar surfaces and the pair of side walls forming a substantially rectangular cross-section of the flattened tip section.

3. A flexible catheter guidewire as recited in claim 2, wherein the pair of planar surfaces are not parallel.

4. A flexible catheter guidewire as recited in claim 3, wherein the flattened tip section comprises a first end and a second end of the tip section decreasing from the first end of the tip section to the second end of the tip section.

5. A flexible catheter guidewire as recited in claim 4, wherein the thickness of the flattened tip section decreases from about 0.0026 inches at a first end thereof to 0.0009 inches at a second end thereof.

6. A flexible catheter guidewire as recited in claim 2, wherein the flattened tip section is about 0.75 inches long and has a thickness in the range of about 0.0009 inches to 0.0026 inches.

7. A flexible catheter guidewire as recited in claim 1, wherein the coil spring comprises a radiopaque material.

8. A flexible catheter guidewire comprising:
   a. an elongate flexible core comprising:
      a main section having a predetermined uniform diameter extending from a proximal end of the guidewire to a distal region of the guidewire;
      a tapered section extending distally from the main section and having a progressively reduced outer diameter;
      a flattened tip extending distally from the tapered section, the flattened tip having a substantially rectangular cross-section, the flattened tip comprising a first end and a second end, the first end of the flattened tip being attached to the tapered section, the thickness of the flattened tip decreasing from the first end of the flattened tip to the second end of the flattened tip;
   b. a coil spring attached to the core wire and disposed around the flattened tip, the coil spring being comprised of a radiopaque material: and
   c. a cylindrical, thin-walled hollow tube attached at one end to the core wire beginning at the tapered section and extending continuously up to the coil spring, where the other end of the thin-walled tube is attached to the core wire, the hollow tube having a substantially uniform inner diameter whereby a gap is formed between an inner surface of the hollow tube and an outer surface of the tapered section in order to provide a desired degree of flexibility and steerability, and the hollow tube having a substantially uniform outer diameter which corresponds to the outer diameter of the main section of the wire in order to provide a continuously and uniformly smooth outer surface along the length of the guidewire from the main section to the coil spring.

9. A flexible catheter guidewire s recited in claim 8, wherein the flattened tip comprises:
   a pair of opposing substantially planar surfaces; and
   a pair of side walls connecting the pair of planar surfaces, the pair of planar surfaces and the pair of side walls forming the substantially rectangular cross-section of the flattened tip.

10. A flexible catheter guidewire as recited in claim 9, wherein the flattened tip is about 0.75 inches long and has a thickness in the range of about 0.0009 inches to.0026 inches.

11. A flexible catheter guidewire comprising:

a. an elongated flexible core wire comprising:

a main section having a predetermined uniform diameter extending from a proximal end of the guidewire to a distal region of the guidewire;

a tapered section extending distally from the main section and having a progressively reduced outer diameter;

a flattened tip extending distally form the tapered section, the flattened tip having a substantially rectangular cross-section, the flattened tip comprising a first end and a second end the first end of the flattened tip being attached to the tapered section, the thickness of the flattened tip decreasing form the first end of the flattened tip to the second end of the flattened tip, the second end of the flattened tip having a thickness in the range of about 0.0008 inches to 0.0010 inches;

b. a coil spring attached to the core wire and disposed around the flattened tip, the coil spring being comprised of a radiopaque material; and c. a cylindrical, thin-walled hollow tube attached at one end to the core wire beginning at the tapered section and extending continuously up to the coil spring, where the other end of the thin-walled tube is attached to the core wire, the hollow tube having a substantially uniform inner diameter whereby a gap is formed between an inner surface of the hollow tube and an outer surface of the tapered section in order to provide a desired degree of flexibility and steerability, and the hollow tube having a substantially uniform outer diameter which corresponds to the outer diameter of the main section of the core wire in order to provide a continuously and uniformly smooth outer surface along the length of the guidewire from the main section to the coil spring.

12. A flexible catheter guidewire as recited in claim 11, wherein the pair of side walls of the flattened tip are substantially formed by a [curvilinear] surface generally perpendicular tot he pair of planar surfaces.]

\* \* \* \* \*

UNITED STATES PATENT AND TRADEMARK OFFICE
CERTIFICATE OF CORRECTION

PATENT NO. : 5,957,865

DATED : September 28, 1999

INVENTOR(S) : Kent Backman, Jerrold Foote

It is certified that error appears in the above-identified patent and that said Letters Patent is hereby corrected as shown below:

Col. 2, ln. 16: after "the" and before "tapered" delete [the]

Col. 2, ln. 37: after "within" and before "blood" insert --a--

Col. 4, ln. 43: after "FIG." change "2" to "1"

Col. 4, ln. 56: after "No." change "304" to --304--

Col. 5, ln. 57: after "of the" change "coil" to --core--

Col. 5, ln. 57: after "wire" change "20" to --12--

Col. 6, ln. 2: after "portion" change "32" to --37--

Col. 8, ln. 26: after "core" and before "comprising" insert --wire--

Col. 8, ln. 54: after "the" and before "wire" insert --core--

Col. 8, ln. 57: after "guidewire" change "s" to --as--

Col. 9, ln. 2: before "flexible" change "elongated" to --elongate--

Col. 9, ln. 8: after "distally" change "form" to --from--

Col. 9, ln. 13: after "decreasing" change "form" to --from--

UNITED STATES PATENT AND TRADEMARK OFFICE
CERTIFICATE OF CORRECTION

PATENT NO. : 5,957,865

DATED : September 28, 1999

INVENTOR(S) : Kent Backman, Jerrold Foote

It is certified that error appears in the above-identified patent and that said Letters Patent is hereby corrected as shown below:

Col. 10, ln. 19: after "perpendicular" change "tot he" to --to the--

Col. 10, ln. 19: after "surfaces." delete  --] --.

Signed and Sealed this

Thirty-first Day of October, 2000

Attest:

Q. TODD DICKINSON

Attesting Officer      Director of Patents and Trademarks